United States Patent
Law

(10) Patent No.: US 7,166,279 B2
(45) Date of Patent: Jan. 23, 2007

(54) MYOBLAST TRANSFER THERAPY FOR RELIEVING PAIN AND FOR TREATING BEHAVIORAL AND PERCEPTIVE ABNORMALITIES

(76) Inventor: Peter K. Law, c/o Cell Therapy Research Foundation, 1770 Moriah Woods Blvd., Suite 18, Memphis, TN (US) 38117

( * ) Notice: Subject to any disclaimer, the term of this patent is extended or adjusted under 35 U.S.C. 154(b) by 23 days.

(21) Appl. No.: 09/986,344

(22) Filed: Nov. 8, 2001

(65) Prior Publication Data

US 2002/0044925 A1   Apr. 18, 2002

Related U.S. Application Data

(63) Continuation of application No. 09/132,321, filed on Aug. 11, 1998, now abandoned.

(60) Provisional application No. 60/055,199, filed on Aug. 11, 1997.

(51) Int. Cl.
*A61K 48/00* (2006.01)
*C12N 5/10* (2006.01)

(52) U.S. Cl. .................. 424/93.21; 435/366; 424/93.2

(58) Field of Classification Search ............... 424/93.2, 424/93.1, 93.21; 435/320.1, 325, 455
See application file for complete search history.

(56) References Cited

FOREIGN PATENT DOCUMENTS

| WO | WO 91/02745 | 3/1991 |
| WO | WO 92/16547 | 10/1992 |
| WO | WO 96/18303 | 6/1996 |

OTHER PUBLICATIONS

Deglon et al. Human Gene Therapy 7:2135-2146, 1996.*
Law et al. Cell Transplantation 2:485-505, 1993.*
Allen and Rankin. Proceedings of the Experimental Biology and Medicine 194:81-86, 1990.*
Morris and Herz (Naunyn Schmiedebergs Arch Pharmacol 336:240-243, 1987 (abstract only).*
Beutler et al. "Retrovirus-mediated expression of an artificial beta-endorphin precursor in primary fibroblasts," J. Neurochem. 64(2): 475-481, 1995.*
Skuk, D., "Myoblast transplantaion for inherited myopathies: a clinical approach," Expert Opin. Biol. Ther. 4 (12): 1871-1875, 2004.*
Satoh et al., Myotubes can be formed within implanted adipose tissue, Transplant. Proc. 24(6): 3017-3019, 1992.*
Takeuchi, T., et al., "Production of a Therapeutic Peptide Enkephalin from a Variety of Non-Endocrine Cell Lines Using a Novel Expression Vector for Fusion Peptides," Gene Therapy, vol. 2, pp. 689 (1995).
Sandra, A., "Reversal by Insulin of Concanavalin A Inhibition of Myotube Formation and Evidence for Binding Sites," Endocrinology, vol. 105, No. 2, pp. 391-401 (Aug. 1979).
Wu, et al., "Implantation of AtT-20 or Genetically Modified AIT-20/hENK Cells in Mouse Spinal Cord Induced Antinociception and Opioid Tolerance," Journal of Neuroscience, vol. 14, No. 8, pp. 4806-4814 (1994).

* cited by examiner

*Primary Examiner*—Scott D. Priebe
(74) *Attorney, Agent, or Firm*—Marvin A. Motsenbocker

(57) ABSTRACT

An analgesic benefit is realized by continuously supplying a peptide in vivo that activates an opioid receptor or that interferes with the binding of substance P to its receptors. The long-term, continuous provision of such a peptide can be accomplished by (a) transducing myogenic cells with DNA expressing the peptide and (b) administering the transduced myogenic cells to a patient, such that the cells continuously produce the peptide.

19 Claims, No Drawings

MYOBLAST TRANSFER THERAPY FOR RELIEVING PAIN AND FOR TREATING BEHAVIORAL AND PERCEPTIVE ABNORMALITIES

This application is a continuation of application Ser. No. 09/132,321 filed Aug. 11, 1998, now abandoned, which is based on Provisional Application No. 60/055,199 filed Aug. 11, 1997.

BACKGROUND OF THE INVENTION

The present invention relates to an approach for relieving pain and for treating behavioral and perceptive abnormalities, by using myoblast transfer therapy to provide a long-term, continuous supply of peptides in vivo that have analgesic activity.

Modern analgesia theory advanced significantly with a proposal by Pomeranz et al., *Exp. Neurol.* 54: 172 (1977), that a morphine-like, pituitary peptide mediates acupuncture analgesia. Electroacupuncture was found to reduce responses in spinal cord neurons to noxious stimuli in anesthetized cats and to increase squeak threshold in awake mice. The observed, prolonged time course implicated a hormonal mechanism for the response. Spinal transaction, decerebration or hypophysectomy eliminated this acupuncture effect, and intravenous injections of naloxone, a morphine antagonist, also reduced it markedly.

These results indicate that electroacupuncture stimulates sensory nerves which activate the pituitary glands to release morphine-like hormones (peptides) effecting prolonged reduction in transmission along nociceptive pathways. This mechanism is believed to be a principal mediator of generalized and localized analgesia.

Morphine-like peptides have been identified, and receptors to morphine-like peptides and to other opioid peptides have been found in the brain, the gut, the pituitary gland, the pancreas and the placenta. Hughes et al., *Nature* 258: 577 (1975); Pert et al., *Science* 179: 1011 (1979). These peptides now are known as β-endorphins and enkephalins. Cooper et al., THE BIOCHEMICAL BASIS OF PHARMACOLOGY, 4th ed. (Oxford University Press, New York 1982). Furthermore, stimulation of brain neurons with an opioid peptide such as an endorphin produces analgesia. Fields et al., *Ann. Rev. Physiol.* 40: 217 (1978). This effect can be reversed by naloxone.

Opioid peptides, especially β-endorphins, are essentially neural hormones or transmitters which reach all body tissue through diffusion. The presence of endorphin receptors in large numbers at different areas of the diencephalon and cerebral cortex suggests that the conjugate opioid peptides play a role in analgesia which goes beyond chat of a simple modulator of pain perception. Covenas et al. *Neuropeptides* 30: 261 (1996); Bernstein et al., *Neurosci. Lett.* 215: 33 (1996); Bianchi et al., *Brain Res. Bull.* 40: 269 (1996). Indeed, increases in cerebrospinal fluid and plasma levels of β-endorphins have been shown to modulate and optimize behavioral patterns exhibited in patients suffering from stress, psychiatric disorders, alcoholism, drug addition, obesity, and diabetes. Ryu et al., *Am. J. Chin. Med.* 24: 193 (1996); Odagiri et al., *Int. J. Sports Med.* 17: 325 (1996); Dalayeun et al., *Biomed. Pharmacother.* 47: 311 (1993); Gianoulakis et al., *J. Psychiatry Neurosci.* 18: 148 (1993). These increases also promote natural killer cell mediated cytotoxicity. Jonsdottir et al., *Regul. Pept.* 23: 113 (1996); Sacerdote et al., *Regul. Pept.* 63: 79 (1996).

Analgesia also is affected by binding of a pain mediator called "substance P" to its receptor. There are many similarities between the terminals of opioid neurons and the terminals of substance P sensitive neurons. For example, both types of terminals mediate pain sensation in the spinal cord. Jessel et al., *Nature* 268: 549 (1977). As indicated, for example, in Japanese patent document JP 3133998, substance P receptors have been shown to act as analgesics by masking the activity of substance P. According to PCT application WO 92/16547, the NK-1 receptor preferentially binds substance P and can be used to treat pain, inflammatory disease, mental illness and stress.

Patients afflicted with conditions such as stress, psychiatric disorders, alcoholism, drug addition, obesity, and diabetes may obtain some measure of relief from an above-normal level of endogenous opioid peptides in their plasma. Clinical relief of symptoms of these conditions have been associated with the binding of opioid peptides with their receptors, which is directly correlated with the level of opioid peptides in the patient's plasma and cerebrospinal fluid. Patients also may benefit from increased levels of substance P receptors or substance P analogs. See WO 92/16547, supra, and PCT application WO 91/02745. To date, no adverse reaction has been associated with physiological increases in plasma or cerebrospinal fluid levels of β-endorphins, enkephalins or substance P receptors.

The use of drugs to increase the production and/or secretion of opioid peptides may provide temporary relief, but uncontrollable drug metabolism and rough dosage eventually will overtax the "sick" neurons and their counterparts. Furthermore, the side effects of drugs are numerous and undesirable. Opioid peptides themselves and opioid peptide receptors have been administered as sedatives and analgesics, see U.S. Pat. No. 4,123,523, but the effects of such administrations are short-lived.

Xenogeneic tumor cells secreting β-endorphin have been transplanted into spinal cord cerebro-spinal fluid space of rats, producing analgesic effects. Saitoh et al., *Cell Trans.* 4 (Supp. 1): S13-7 (1995). The transplanted cells were reported to survive for one month, and in vitro studies indicated that the cells would secrete β-endorphin for one month. AtT-20 cells and AtT-20/hENK cells, which secrete β-endorphin and enkephalin, respectively, were implanted into mouse spinal subarachnoid space to investigate their use as a therapy for pain. Wu et al., *J. Neurosci.* 14 (8): 4806 (1994); *J. Neural Transplant. Plast.* 4 (1): 15 (1993). But these procedures are very invasive and therefore very dangerous, since they involve the transplantation of cells directly into cerebrospinal fluid or spinal subarachnoid space. Also, only a limited number of cells are transplanted, making the amount of opioid peptide provided by these methods limited.

A need therefore exists for a method of long term analgesia by supplying a peptide that binds to opioid receptors or that interferes with binding of substance P to its receptors in vivo over a long time period. Such a method would be useful for treating chronic pain and psychiatric conditions that involve abnormal perception, such as depression, chronic anxiety syndromes, paranoia, alcoholism, and drug addiction, and other diseases in which opioid neurons and substance P terminals play a role.

SUMMARY OF THE INVENTION

Accordingly, it is an object of the present invention to provide a method of treating psychiatric conditions that involve abnormal perception, such as depression, chronic anxiety syndromes, paranoia, alcoholism, and drug addiction, chronic pain, and other diseases in which opioid neurons and substance P sensitive neurons play a role. It is also an object of the present invention to provide a composition for performing this method.

In accordance with this and other objects of the invention, there is provided a method of continuously supplying in vivo a peptide that can bind to opioid receptors or that can interfere with binding of substance P to its receptor comprising the steps of (a) transducing myogenic cells with DNA encoding the peptide, and (b) administering the transduced myogenic cells to a patient, such that the cells continuously produce the peptide. In one embodiment, the analgesic peptide is selected from the group consisting of an opioid peptide, a polypeptide that binds substance P and a substance P analog. In one embodiment, the myogenic cells are selected from the group consisting of myoblasts, myotubes, and muscle cells. In another embodiment, the cells are transduced with DNA encoding multiple copy sequences of the peptide separated by cleavage sites. In another embodiment, the transduced cells are administered by intramuscular injection into a paraspinal muscle of the patient. In yet another embodiment, large chondroitin-6-sulfate proteoglycan or insulin is administered with the transduced myogenic cells. Co-administration of an immunosuppressant also is preferred in some embodiments.

The invention also provides a method of continuously supplying in vivo a naturally occurring analgesic peptide comprising the steps of (a) transducing myogenic cells with DNA containing a promoter for an endogenous structural gene encoding the peptide, and (b) administering the transduced myogenic cells to a patient, such that the cells continuously produce the peptide.

The invention further provides a composition for continuously supplying in vivo a peptide that binds an opioid receptor or that interferes with binding of substance P to its receptor, comprising the steps of (a) transducing myogenic cells that contain heterologous DNA and that express the peptide, and a pharmaceutically acceptable carrier. In one embodiment, the heterologous DNA comprises a gene encoding the peptide and a promoter. In another embodiment, the heterologous DNA comprises a promoter for an endogenous structural gene encoding the peptide. In another embodiment, the composition additionally comprises large chondroitin-6-sulfate proteoglycan or insulin.

Additional objects and advantages of the invention are set forth in part in the description that follows, and in part will be obvious from the description, or may be learned by practice of the invention.

DETAILED DESCRIPTION OF PREFERRED EMBODIMENTS

It has been discovered that genetically transduced myogenic cells can be employed to provide a long-term, continuous supply of a peptide having analgesic activity. This method is useful for treating chronic pain as well as psychiatric conditions that involve abnormal perception, such as depression, chronic anxiety syndromes, paranoia, alcoholism, and drug addiction, and other diseases in which neurons that bind opioids and/or neurons that bind substance P play a role. Such conditions have not been treated heretofore by long-term administration of analgesic peptide in vivo.

Analgesic peptides suitable for the invention are peptides that bind opioid receptors or that interfere with binding of substance P to its receptor. Among these peptides are opioid peptides, polypeptides that bind substance P, and peptides that are substance P analogs. In this context, the phrase "polypeptide that binds substance P" denotes a peptide or protein that has affinity for substance P such as, for example, substance P receptor protein or a peptide or peptide analog derived from this receptor and that retain the ability to bind substance P. Such peptides and proteins bind substance P and thereby interfere with the binding of substance P with its receptor. The skilled artisan can test binding to substance P with an assay. Substance P analogs act as analgesics by interfering with binding between substance P and its receptor. For example, PCT application WO 91/02745, supra, discloses analogs that do not exhibit the natural activity of substance P but that act as competitive inhibitors of substance P.

In accordance with the invention, myogenic cells are transduced ex vivo so that they express at least one of the above-enumerated peptides, either while in cell culture, or after differentiation in vivo. Cells that have been transduced with a gene encoding such a peptide are administered to the patient, for example, by injection into muscle or adipose tissue of the patient. The transduced cells can survive and grow in the recipient tissue. For example, cells injected into muscle tissue can form myotubes and mature into muscle fibers. Cells injected into adipose tissue can survive and be converted into fat cells. Transduced cells injected into both types of tissue can express the desired analgesic peptide continuously. The expressed peptide exits the cell and travels through the blood to other areas of the body, including the spinal cord and brain.

Myoblast transfer therapy (MTT) has been used to treat muscle weakness and degeneration and is a useful technique for administering cells that express an analgesic peptide. See U.S. Pat. No. 5,130,141, the contents of which are incorporated herein by reference. In accordance with this method, genetically normal myogenic cells are administered to a myopathic muscle of the patient, thereby increasing muscle function, locomotive patterns and respiratory function. Normal myoblast transfer therapy has been shown to produce the missing protein dystrophin for up to six years in Duchenne muscular dystrophy patients. Law et al., *Cell Transplantation* 6: 95–100 (1997).

Although early myoblast transfer studies used muscle as the recipient tissue, other tissues also can be used. For example, myoblasts can grow after their injection or surgical implantation into adipose tissue, as described by Satoh et al., *Transplantation Proceedings* 24: 3017–19 (1992).

Myoblasts have been transduced with genes for Factor IX, erythropoietin (EPO), and human growth hormone, and the Fas ligand to increase circulating levels of these proteins. Thompson, *Thromb. and Haemost.* 74(1): 45 (1995); Hamamori et al., *J. Clin. Invest.* 95: 1808 (1995), and *Human Gene Therapy* 5: 1349 (1994); Barr et al *Science* 254: 1507 (1991); Dhawan et al., *Science* 254: 1509 (1991); Lau et al., *Science* 273: 109 (1996). The success of these methods has varied. According to Thompson (1995), for instance, preliminary data suggest that human myoblasts removed from the body survived less well in culture and progressively lost their ability to express factor IX. Lau et al. (1996), reports that expression of the Fas ligand was local and appeared to cease after 80 days. On the other hand, Hamamori et al. (1994) reports that the in vivo implantation of a stable, high level, EPO-producing muscle cell clone resulted in sustained high serum EPO levels for three months, and Dhawan et al. (1991) states that transduced myoblasts continued to secrete hGH after they differentiated into myotubes, with no difference in secretion levels between myoblasts and myotubes.

Transduced myoblasts have not been used previously to supply an analgesic peptide continuously in vivo, however.

Furthermore, although gene therapy has been studied as a means of supplying opioid peptides in vivo, the transduced cells were injected directly into spinal cord, cerebro-spinal fluid or spinal subarachnoid space. Saitoh et al., *Cell Trans.* 4 (Supp. 1): S13-7 (1995); Wu et al., *J. Neurosci.,* 14(8): 4806 (1994); Wu et al., *J. Neural Transplant. Plast.* 4(1): 15 (1993). As discussed above, these methods are very invasive, only a limited number of cells are transplanted, and the transduced cells expressed the opioid peptides for only one month. In accordance with the present invention, by contrast, the transduced myoblasts are not injected into the central nervous system. Moreover, unlike the short-term expression of opioid peptides effected in conventional gene therapies, the present invention provides a continuous, long-term supply of opioid peptides which lasts, for example, up to at least six years. These aspects of the present invention represent distinct advantages that have not been appreciated.

Myogenic cells that are suitable for the present invention include myoblasts, myotubes, and muscle fiber cells. Myoblasts are particularly preferred, in accordance with one embodiment of the invention. Myoblasts are mononuclear embryonic muscle cells that differentiate into multinucleated myotubes. Each nucleus of a myoblast contains over 100,000 genes, including genes for opioid peptides such as β-endorphins and enkephalins. Myoblasts divide extensively, migrate, fuse naturally to form syncytia, lose MHC-1 antigens soon after fusion, and constitute about 50% of the dry body weight of humans. Myoblasts are unusual in that they are capable of natural cell fusion among themselves and with mature muscle fibers. As a result of this fusion, a transduced myoblast transfers its nucleus and therefore all of its genes to the cell with which it fuses, which may be a genetically normal or an abnormal muscle cell.

Myogenic cells, such as allogenic cells, can be obtained from a patient to be treated, from a relative, or from another human, or cells may be obtained from another animal donor. In a typical procedure, 1 to 2 grams of skeletal muscle are harvested from a donor. Myogenic cells also can be cultured or produced by cloning methods known to those skilled in the art as shown, for example, in U.S. Pat. No. 5,130,141.

In accordance with one embodiment of the invention, muscle cells from a human or animal donor are stimulated 0–3 days before harvesting to produce a reservoir of satellite cells that are myoblast reserves in mature muscles. The myogenic cells can by stimulated by, for example, injuring the cells with a number of needle probings, or by sonication.

In accordance with one embodiment of the invention, harvested cells are processed to obtain a pure culture of myoblasts. See Law et al. *Cell Transplant.* 1: 235 (1992); *Cell Transplant.* 2: 485 (1993); *Muscle and Nerve* 11: 525-33 (1988). For example, a muscle biopsy is dissociated with 0.1% collagenase and 0.2% crude trypsin in phosphate buffered saline at pH 7.3. The mixture is stirred for 45 minutes, with three changes of enzyme solution alternated with three changes of a neutralizing medium comprising 100 parts Dulbecco's modified Eagle's Medium (DMEM, Gibco) containing 0.37% $NaHCO_3$ and 4 mM glutamine; 10 parts horse serum and 1% antibiotic-anti-mycotic.

Pursuant to one embodiment of the present invention, the harvested myogenic cells are transduced ex vivo with DNA encoding a peptide that either binds an endorphin receptor or that inhibits binding of substance P to its receptor. Peptides that are known to have suitable activity in this context are β-endorphin, α-endorphin, gamma-endorphin, delta-endorphin, Met sup 5 (a five amino acid residue peptide with endorphin-like activity), active endorphin peptides comprising parts of the β-endorphin sequence, enkephalin, an NK-1 receptor, a polypeptide that binds substance P, or a substance P analog that competitively inhibits the binding of substance P to its receptor. The phrase "substance P analog" denotes a peptide that comprises the five carboxy-terminal amino acid sequence of substance P and that binds to the substance P receptor, inhibiting substance P activity. See Payan, *Ann. Rev. Med.* 40: 341 (1989), and PCT application WO 91/02745.

Additional peptides can be found by kinetics experiments that reveal whether a given peptide either binds to an opioid receptor or competes for binding between substance P and its receptor. These experiments can be done routinely. See, for example, PCT application WO 92/16547.

DNA sequences useful for the invention are known or can be designed by those skilled in the art from known amino acid sequences of the peptides. For example, Saitoh et al., *Cell Trans.* 4 (Supp. 1): S13-7 (1995), discloses a DNA sequence that codes for β-endorphin; Wu et al. (1993, 1994), supra, disclose sequences for β-endorphin and enkephalin; U.S. Pat. No. 4,123,523 discloses amino acid sequences of β-endorphin peptides; PCT application WO 92/16547 discloses a gene encoding the substance P receptor NK-1; Japanese patent document JP 3133998 discloses the amino acid sequence of a substance P receptor; and PCT application WO 91/02745 discloses the amino acid sequences of several substance P analogs, such as deletion and addition mutants of substance P.

In accordance with one embodiment of the invention, the DNA encodes a plurality of copies of a peptide that produces analgesia. In a preferred embodiment the peptide is an opioid peptide and regions of the DNA that code for multiple copies are separated by cleavage sites (see PCT application WO 96/17941). This embodiment can provide an amplified amount of a naturally occurring peptide.

The transduction of myogenic cells with a DNA sequence can be effected via known methods, such as those reported by Thompson (1995) and Hamamori et al. (1995), supra. Generally, a DNA construct is used that contains a promoter upstream of the structural gene that encodes the desired peptide. Suitable promoters are described, for example, in U.S. Pat. No. 5,618,698.

According to another embodiment of the present invention, the harvested myogenic cells are transduced ex vivo with a DNA containing a promoter that can link up with and function (i.e., turn on or increase expression) with an endogenous gene within the nucleus of a myogenic cell. In this embodiment, DNA comprising a regulatory sequence, an exon and a splice donor are introduced into a cell by homologous recombination into the cell's genome at a preselected site. The introduction of this DNA results in the production of a new transcription unit in which the regulatory sequence, exon and splice donor site are operatively linked to the endogenous gene.

The introduction of DNA typically is followed by selection of cells that have received a promoter in a desired location, to turn on the desired gene. Applicable selection methodology is described, for instance, in U.S. Pat. Nos. 5,641,670 and 5,272,071. Selection techniques also are described by Mansour et al., *Nature* 136: 348, 349 (1988). After selection, the cells which express the desired gene are cultured and then introduced into a patient.

The transduced myogenic cells are cultured to produce a sufficient quantity of cells for administration to the patient by any of a variety of methods known in the art. For example, see Law et al. (1988, 1992), supra. The amount of cells cultured will depend on the condition of the patient and the severity of the disease being treated. For example, from about 1 billion to about 100 billion myoblasts can be cultured for administration to a patient. In accordance with one embodiment of the invention, cells are cultured in the neutralizing medium described above, supplemented with two parts of chick embryo extract. Cells are fed fresh growth medium every two days, and are incubated in 7% $CO_2$ at 37° C. for 35–40 days.

In accordance with one embodiment of the invention, the transduced cells are administered to the patient by intramuscular injection. Law et al., *Cell Transplant.* 1: 235 (1992); loc. cit. 2: 485 (1993); Law et al. *Exp. Neurol., Transplant Proc.* 29: 2234 (1997). The amount of opioid peptides provided in accordance with the present invention can be controlled by selecting the number of muscles injected and the number of cells injected. In accordance with one embodiment of the invention, the direction of injection is controlled to optimize the number of transduced cells delivered to recipient muscle fibers. For example, injecting the administered cells diagonally through muscle fibers has been shown to maximize the resulting number of muscle fibers fused with administered cells.

Pursuant to another embodiment of the invention, transduced cells are administered to specific muscles which help target the cells to a location between laminae IV and V of the spinal cord. For example, the transduced cells can be injected into paraspinal muscles or neck muscles, such as the levator scapulae. Although transduced myogenic cells administered anywhere in the body will secrete peptides that will travel through the blood and reach the spinal receptors, targeting the administration of the cells to paraspinal muscles or neck muscles that are in proximity to the spinal cord is expected to result in more peptides reaching the receptors more rapidly, thereby increasing the efficacy of the method.

The transduced cells also may be administered by surgical implantation into the patient. The cells can be implanted in, for example, adipose tissue.

In a further embodiment, the patient also is given an effective amount of an immunosuppressant to minimize rejection of the transduced cells. See U.S. Pat. No. 5,130,141 and Law et al. (1992, 1993), supra. For example, cyclosporin A, another immunosuppressant, or combinations of immunosuppressants, can be given in accordance with known procedures. Suitable dosage forms, dosage amounts and dosing schedules are known in the art. For example, cyclosporin A can be given orally in a daily dose of about 7 mg/kg body weight. A typical dosing schedule comprises giving the daily dose in two divided doses, and the patient's whole blood can be monitored to maintain a trough level of about 250 mg/ml cyclosporin A.

In accordance with one embodiment of the invention, fusion of the transduced myoblasts is facilitated by administration of large chondroitin-6-sulfate proteoglycan (LCSP) as described in the above-cited U.S. application Ser. No. 08/477,377, now abandoned. Trauma from injecting myoblasts into the extracellular matrix triggers the release of basic fibroblast growth factor and large chondroitin-6-sulfate proteoglycan. These released molecules stimulate myoblast proliferation. Increasing the level of large chondroitin-6-sulfate proteoglycan at the injection site facilitates myoblast fusion and proliferation. According, in accordance with one embodiment of the invention, large chondroitin-6-sulfate proteoglycan preferably is administered with the transduced myoblasts.

In accordance with one embodiment of the invention, the large chondroitin-6-sulfate proteoglycan is under-sulphated. See Hutchison et al., *Devel. Biol.* 115: 78–83 (1986). Large chondroitin-6-sulfate proteoglycan is believed to be synthesized in an under-sulphated form pre-fusion, but becomes more highly sulphated post-fusion. Id. As used here, therefore, the phrase "under-sulphated large chondroitin-6-sulfate proteoglycan" denotes a degree of sulphation that is about the same as that observed in naturally occurring large chondroitin-6-sulfate proteoglycan from cells just before fusion. In accordance with this aspect of the invention under-sulphated large chondroitin-6-sulfate proteoglycan is administered at a concentration between about 5 μM to about 5 mM. Chondroitin-6-sulfate can be administered together with the transduced cells, or can be given in a separate formulation as a separate injection.

Insulin also facilitates proliferation of myoblasts and promotes myotube development. In accordance with one aspect of the invention, therefore, insulin is administered with the transduced myocytes. For example about 0.2 mM of insulin can be given, either as part of the same formulation as the cells, or as a separate formulation, given, for example, in a separate injection.

In accordance with one embodiment of the invention, undesirable effects from over-production of the desired peptide are regulated with agonists such as naloxone or SP-40,40. Pomeranz et al., *Altern. Thor. Health Med.* 2: 85 (1996); Choi-Miura et al., *Biol. Pharm. Bull.* 16: 228 (1993); Pomeranz et al., *Exp Neurol.* 54: 172 (1977). For example, if the endogenous level of the peptide becomes too high, naloxone or SP-40,40 can be administered to counteract the peptide's effects. Typical symptoms of over-production of an analgesic peptide include extreme drowsiness, low respiratory rate, cyanosis, low blood pressure symmetrical, pinpoint pupils, and depressed urine formation. A usual course of naloxone treatment involves giving small intravenous or intramuscular doses of naloxone (about 0.4 mg to about 0.8 mg). Symptoms frequently improve after the first dose, but can be repeated after 2–3 minutes, up to a total dose of about 10 mg.

As discussed above, the administration of transduced myogenic cells in accordance with the present invention provides a continuous, long-term supply of an analgesic peptide in vivo. The peptide travels from the site of synthesis such as from muscle or adipose tissue and reach sensory nerve endings, the spinal cord and brain, where it combines with nerve cell receptors to produce analgesia. Analgesia produced by the peptide is useful for treating chronic pain and psychiatric conditions that involve abnormal perception, such as depression, chronic anxiety syndromes, paranoia, alcoholism, and drug addiction, and other diseases in which opioid neurons and substance P terminals play a role. The continuous long-term supply of an analgesic peptide in vivo as a medical treatment offers a novel methodology of treating these conditions.

The invention also provides a composition that makes an analgesic peptide that binds to opioid receptors or interferes with binding of substance P to its receptor in vivo. In one embodiment, the composition comprises myogenic cells containing heterologous DNA coding for an analgesic peptide together with one or more pharmaceutically acceptable carriers.

Examples of suitable pharmaceutical carriers include diluents, solvents, buffers, and/or preservatives. An example of a pharmaceutically acceptable carrier is phosphate buffer that contains NaCl. Other pharmaceutically acceptable carriers include aqueous solutions, non-toxic excipients, salts, preservatives, buffers and the like, as described in REMINGTON'S PHARMACEUTICAL SCIENCES, 15 th Ed. Easton: Mack Publishing Co., pages 1405–1412 and pages 1461–1487

(1975), and THE NATIONAL FORMULARY XIV., 14th Ed. Washington: American Pharmaceutical Association (1975). Examples of nonaqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobials, anti-oxidants, chelating agents and inert gases. The pH and exact concentration of the various components of the binding composition are adjusted according to routine skills in the art. See GOODMAN AND GIMMAN'S THE PHARMACOLOGICAL BASIS FOR THERAPEUTICS (7th ed.)

In accordance with one embodiment, the composition comprises transduced myogenic cells, large chondroitin-6-sulfate proteoglycan, and a pharmaceutically acceptable carrier.

In accordance with another embodiment, the composition comprises transduced myogenic cells, insulin, and a pharmaceutically acceptable carrier.

The embodiments of the invention are further illustrated through the following examples which show aspects of the invention in detail. These examples illustrate specific elements of the invention and are not to be construed as limiting the scope thereof.

EXAMPLE 1

Treatment of Patient Suffering from Depression by Injection into Muscle Tissue

The skeletal muscles of a patient suffering from a psychiatric condition involving depression are stimulated by numerous needle probings to produce a reservoir of satellite myoblast cells. Three days later, the patient is placed under general anesthesia, and 2 g of skeletal muscle are harvested from the patient. The harvested muscle is processed to obtain a pure culture of myoblasts. The harvested muscle is dissected free of skin and other tissue and the cells are dissociated with 0.1% collagenase and 0.2% crude trypsin in phosphate buffered saline at pH 7.3. The mixture is stirred for 45 minutes, with three changes of enzyme solution alternated with three changes of a neutralizing medium comprising 100 parts Dulbecco's modified Eagle's Medium (DMEM, Gibco) containing 0.37% $NaHCO_3$ and 4 mM glutamine; 10 parts horse serum and 1% antibiotic-antimycotic.

These myoblasts are transduced with DNA containing a gene for enkephalin and a suitable promoter. The transduced myoblasts then are cultured in the neutralizing medium described above supplemented with 2 parts of chick embryo extract. The cells are fed fresh growth medium every 2 days, and are incubated in 7% $CO_2$ at 37° C. for 40 days, when about 2 billion myoblast cells (progeny of the transduced myogenic cells) are present.

The patient again is placed under general anesthesia and the progeny of the transduced myogenic cells are injected intramuscularly, into paraspinal muscles of the patient. Within one week thereafter, the patient's symptoms should begin to ameliorate.

EXAMPLE 2

Treatment of Patient Suffering from Depression by Injection into Adipose Tissue

Myoblasts are obtained and transduced as described in Example 1 to form about 10 billion progeny myoblast cells. The patient's breast tissue is anesthetized and the cells are injected into the anesthetized tissue. Within one week thereafter the patient's symptoms should begin to ameliorate.

EXAMPLE 3

Treatment of Patient Suffering from Alcoholism

The skeletal muscles of a patient suffering from alcoholism are stimulated by sonication to produce a reservoir of satellite myoblast cells. Three days later, the patient is placed under general anesthesia, and 2 g of skeletal muscle are harvested from the patient. The harvested muscle is processed to obtain a pure culture of myoblasts as described in Example 1 above.

These myoblasts are transduced with DNA containing a promoter for an endogenous β-endorphin gene. The transduced myoblasts then are cultured as described in Example 1 above, until 50 billion cells are obtained.

The patient is again placed under general anesthesia and the progeny of the transduced myogenic cells are injected into paraspinal muscles of the patient.

Within one week after the procedure, the patient's symptoms begin to be relieved.

EXAMPLE 4

Composition For Providing a Long-Term, Continuous Supply of Enkephalin In Vivo

The following composition is provided:
1 billion myogenic cells transduced with DNA that codes for enkephalin; and a phosphate buffer containing NaCl and human serum albumen as a pharmaceutically acceptable carrier.

EXAMPLE 5

Composition For Providing a Long-Term, Continuous Supply of β-Endorphin In Vivo

The following composition is provided:
1 billion myogenic cells transduced with DNA that codes for a promoter of a human endorphin gene; and water as a pharmaceutically acceptable carrier.

It will be apparent to those skilled in the art that various modifications and variations can be made to the processes and compositions of this invention. Thus, it is intended that the present invention cover the modifications and variations of this invention provided they come within the scope of the appended claims and their equivalents.

What is claimed is:

1. A method of supplying to the central nervous system of a human patient a peptide that binds an opioid receptor, comprising:
    (a) obtaining autologous muscle cells from the patient and preparing a pure in vitro culture of myoblasts;
    (b) transducing the culture of (a) with DNA encoding the peptide, such that the myoblasts express the peptide, then
    (c) introducing the transduced myoblasts as a suspension to a muscle of the same human patient in a form that allows fusion with and intracellular expression of the peptide in pre-existing muscle cells of the human patient, the muscle selected from the group consisting of a paraspinal muscle, levator scapulae muscle, muscle between laminae IV and V of the spinal cord and neck muscle, so that the peptide is produced in proximity to the spinal cord of the patient.

2. The method of claim 1, wherein step (a) comprises the mechanical stimulation of the human patient's skeletal muscle tissue to produce a reservoir of satellite myoblast cells prior to removal of the satellite myoblast cells for the in vitro culture.

3. The method of claim 2, wherein the mechanical stimulation is carried out by numerous needle probings or by sonication.

4. The method of claim 2, wherein the satellite myoblast cells are allowed to develop for about 3 days after mechanical stimulation and before their harvest.

5. The method of claim 1, wherein more than 1 billion myoblasts are cultured for administration into the patient.

6. The method of claim 1, wherein step (c) comprises injecting the transduced myoblasts diagonally through muscle fibers.

7. The method of claim 1, wherein large chondroitin-6-sulfate proteoglycan is added to the suspension of myoblasts prior to administering the myoblasts to the patient.

8. The method of claim 7, wherein, large chondroitin-6-sulfate proteoglycan is added to a final concentration of between about 5 micromolar to about 5 millimolar.

9. The method of claim 7, wherein insulin is added to the suspension of myoblasts prior to administrating the myoblasts to the patient.

10. A method of supplying to the central nervous system of a patient a peptide that binds an opioid receptor, comprising:
  (a) obtaining allogenic muscle cells from a human donor and preparing a pure in vitro culture of myoblasts;
  (b) transducing the culture of (a) with DNA encoding the peptide, such that the myoblasts express the peptide, then
  (c) introducing at least 1 billion cells from (b) as a suspension into a patient by surgical implantation, in the presence of large chondroitin-6-sulfate proteoglycan.

11. The method of claim 10, wherein step (a) comprises the mechanical stimulation of a human donor's skeletal muscle tissue to produce a reservoir of satellite myoblast cells prior to removal of the satellite myoblast cells for the in vitro culture.

12. The method of claim 11, wherein the mechanical stimulation is carried out by numerous needle probings or by sonication.

13. The method of claim 11, wherein the satellite myoblast cells are allowed to develop for about 3 days after mechanical stimulation and before their harvest.

14. The method of claim 10, wherein about 10 billion progeny myoblasts are cultured for administration into the patient.

15. The method of claim 10, wherein step (c) comprises injecting the transduced myoblasts diagonally through muscle fibers.

16. The method of claim 10, wherein large chondroitin-6-sulfate proteoglycan is added to the suspension of myoblasts prior to administering the myoblasts to the patient.

17. The method of claim 16, wherein large chondroitin-6-sulfate proteoglycan is added to a final concentration of between about 5 micromolar to about 5 millimolar.

18. The method of claim 16, wherein insulin is added to the suspension of myoblasts prior to administrating the myoblasts to the patient.

19. The method of claim 10, wherein the myoblasts are introduced into adipose tissue.

* * * * *